United States Patent [19]

Schane, Jr. et al.

[11] 4,213,977
[45] Jul. 22, 1980

[54] PITUITARY-ADRENAL INHIBITING METHOD

[75] Inventors: Harry P. Schane, Jr.; Homer R. Harding, both of Canaan; John E. Creange, Kinderhook, all of N.Y.

[73] Assignee: Sterling Drug Inc., New York, N.Y.

[21] Appl. No.: 961,880

[22] Filed: Nov. 20, 1978

[51] Int. Cl.$^2$ ............................................. A61K 31/58
[52] U.S. Cl. .................................................... 424/241
[58] Field of Search .......................................... 424/241

[56] References Cited

U.S. PATENT DOCUMENTS 3,657,435  4/1972  Stonner ................................. 424/241

Primary Examiner—Elbert L. Roberts
Attorney, Agent, or Firm—Theodore C. Miller; B. Woodrow Wyatt

[57] ABSTRACT

The method of suppressing pituitary-adrenal function without producing peripheral glucocorticoid effects in a primate comprising administering to the primate an amount of (17α)-2'-(4-fluorophenyl)-2'H-pregna-2,4-dien-20-yno[3,2-c]-pyrazol-17-ol effective in reducing the concentration of circulating hydrocortisone is disclosed.

2 Claims, 1 Drawing Figure

Effect of Nivazol and Medrol on Circulating Cortisol Levels in the Mature Female Monkey.

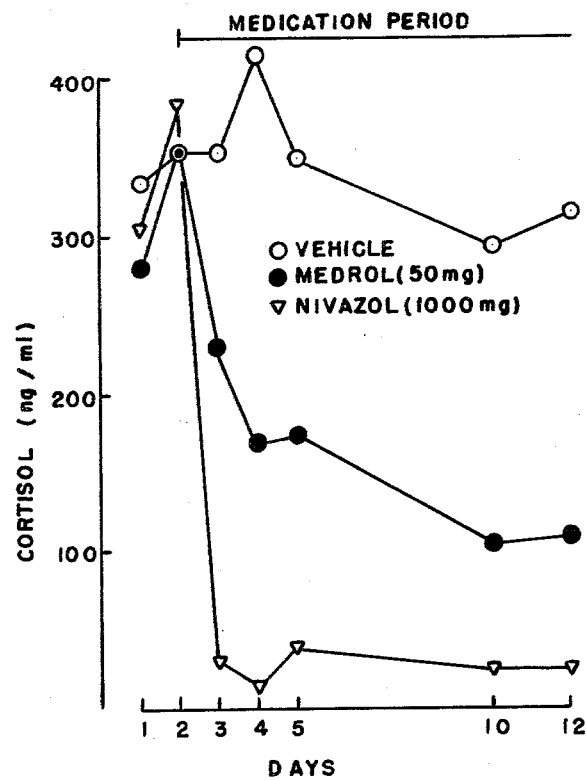
Effect of Nivazol and Medrol on Circulating Cortisol Levels in the Mature Female Monkey.

PITUITARY-ADRENAL INHIBITING METHOD

BACKGROUND OF THE INVENTION

1. Field of the Invention

This invention relates to a method of suppressing pituitary-adrenal function without producing peripheral glucocorticoid effects using a steroid.

2. Description of the Prior Art

17β-Hydroxy-17-ethynyl-4-androstenol[3,2-c]-2'-(p-fluorophenyl)pyrazole having the structural formula

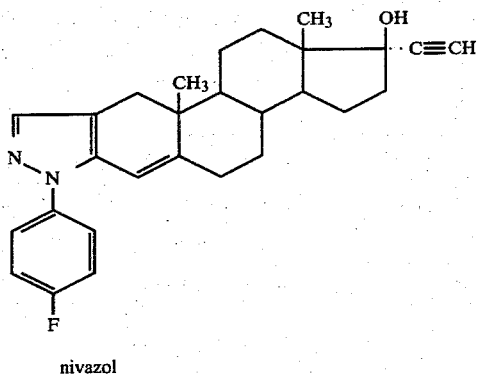

nivazol and glucocorticoid anti-inflammatory properties and compositions thereof are described by Stonner U.S. Pat. No. 3,657,435, issued Apr. 18, 1972. The United States Adopted Name of the steroid of the foregoing structural formula is nivazol and the current Chemical Abstracts name is (17α)-2'-(4-fluorophenyl)-2'H-pregna-2,4-dien-20-yno[3,2-c]pyrazol-17-ol.

SUMMARY OF THE INVENTION

This invention relates to the method of suppressing pituitary-adrenal function without producing peripheral glucocorticoid effects in a primate which comprises administering to the primate an amount of (17α)-2'-(4-fluorophenyl)-2'H-pregna-2,4-dien-20-yno[3,2-c]pyrazol-17-ol effective in reducing the concentration of circulating hydrocortisone.

DETAILED DESCRIPTION OF THE INVENTION INCLUSIVE OF THE PREFERRED EMBODIMENTS

This invention is based on the discovery that nivazol suppresses circulating hydrocortisone (cortisol) levels in the monkey without exhibiting peripheral glucocorticoid activity. In previous studies nivazol had exhibited the complete profile of glucocorticoid activity in rodents, in which it had shown peripheral action as a catabolic and anti-inflammatory agent and central action as an inhibitor of the pituitary-adrenal axis. In three-month toxicological studies in the rat it had shown suppression of body weight gain and adrenal size, evidence for both central and peripheral glucocorticoid activity. However, in three-month toxicological studies in the monkey there had been no evidence of any drug related changes except a slight decrease in adrenal size. In human tolerance studies it had shown marked suppression of urinary corticoid excretion but had been without effect on urine volume, electrolytes, phosphorus and nitrogen. Nivazol was subsequently found to be inactive as an anti-inflammatory agent in humans.

After the discovery of suppression of circulating cortisol levels in the monkey further studies were undertaken to confirm the apparently different activity profiles of nivazol in rodents and primates. The glucocorticoid activity profile of nivazol in the rat was confirmed. In monkeys, nivazol diminished levels of circulating cortisol and therefore is an inhibitor of the pituitary-adrenal axis, but did not affect levels of eosinophils and fasting blood glucose and therefore does not have peripheral glucocorticoid effects. As an apparent direct inhibitor of ACTH and, thus, an indirect inhibitor of adrenal corticoid output, nivazol has potential application in several problems of human medicine.

Post-traumatic states are characterized by prolonged increased corticoid output and a resultant catabolism. There is both increased nitrogen loss and the development of electrolyte imbalances as well as higher incidence of ulcers. Therefore, modulation of adrenal output to re-establish appropriate adrenal function after the initial response is considered therapeutically sound. Nivazol, by reducing ACTH production, provides a method to control adrenal function.

Certain patients with endogenous depression have been identified as having a flattening of the circadian plasma cortisol levels. In these individuals, the normally low night-time values are elevated while the high morning circulating levels are essentially unchanged. The 24-hour urinary free cortisol levels are correspondingly elevated. This distortion in the secretory pattern cannot be attributed to a simple stress response, since the hypersecretion persists during levels of sleep, can occur with little evidence of affective arousal and is not corrected with sedative medication. While the specific inter-relationships between the pituitary-adrenal axis and depression are not known, it has been suggested that the imbalance is due to hypersecretion of ACTH.

Nivazol might also be used in combination with trilostane (United States Adopted Name for 4α,5-epoxy-17β-hydroxy-3-oxo-5α-androstane-2α-carbonitrile, adrenocortical suppressant and abortifacient) to reduce adrenal steroid output without evoking compensatory pituitary response.

BIOLOGICAL TESTS

Materials and Methods

In the tests described below 6β-methylprednisolone (Medrol ®) was used as the glucocorticoid standard of comparison.

Mature male and female rats of the Sprague-Dawley strain were obtained from the Charles River Breeding Laboratories. Mature female rats weighing an average of 203 g. were medicated orally with nivazol, Medrol or vehicle for 14 consecutive days. Initial and final weights were determined. On the day following the last medication, the rats were killed and the thymus, adrenals and pituitary of each rat were removed, cleaned and weighed. Feed consumption was also determined throughout the study.

Five days after bilateral adrenalectomy, male rats were medicated orally with nivazol, Medrol or vehicle for 5 consecutive days. The rats were weighed initially and on the afternoon of the 4th day of medication and fasted from 4 P.M. that day until autopsy. On the day of autopsy (5th medication day), the animals were medicated at 7 A.M. and 7 hours later were anesthetized with sodium pentobarbital. A section of liver was removed, weighed and prepared for glycogen determination as described by Seifter, Dayton, Novic and Muntcuyler (Arch. Biochem. 25, 191, 1950). The thymus of each rat was removed and weighed. Where appropriate, the potency of nivazol was compared with Medrol using regression analysis.

Two studies were undertaken in the mature female rhesus monkey (*Macaca mulatta*). In both studies, eosinophil counts were done on the day before treatment started and the monkeys were grouped to provide a uniform mean eosinophil count. To reduce the effects of a wide variance in eosinophil counts, the eosinophil index ($\sqrt{x+1}$, where x = the number of eosinophils/$\mu$l) was used.

In the first study, the monkeys were medicated orally with nivazol at doses of 0, 50, 100 or 200 mg/monkey/day for 18 consecutive days. Circulating cortisol levels and eosinophil counts were determined throughout the study and fasting blood glucose was evaluated prior to the initiation of the study and 6 hours after the last medication.

In the other study, the monkeys were medicated orally with nivazol (1000 mg/monkey), Medrol (50 mg/monkey) or vehicle (20 ml/monkey) for 15 consecutive days. Throughout the study, circulating cortisol levels were determined in morning plasma samples and blood was also drawn for eosinophil counts approximately 4 hours after medication. On the 7th and 15th days of the study, the monkeys were fasted overnight and blood glucose determined 6 hours after medication. The fasting blood glucose levels were also determined 8 days after the last medication.

Nivazol and Medrol (obtained from commercial sources as 4 or 8 mg. tablets) were prepared as solution/suspensions in a gum tragacanth: water (1:99, w/v) vehicle and administered by gavage.

Results

Table 1 summarizes the results seen when nivazol, Medrol or vehicle was administered orally to mature female rats for 14 consecutive days. With both steroids, there were dose-related decreases in the weights of the thymus and adrenals and a decreased body weight gain without effect on daily feed consumption. Nivazol was estimated to be 0.4 times (95% confidence limits 0.05-1.2) as potent as Medrol using body weights as an index of glucocorticoid activity. While potency estimates using the organ weights were not applicable since the dose response curves were significantly non-parallel, the potencies of these two agents are not markedly different.

Table 2 presents data obtained following the oral administration of nivazol or Medrol to adrenalectomized rats for 5 days. Treatment with dose levels of 5 and 15 mg/kg/day produced similar dose-related decreases in thymus weight and increases in liver glycogen with both steroids.

Nivazol was administered orally to mature rhesus monkeys over a dosage range of 50 to 200 mg/monkey/day for 18 days. There was a significant decrease in circulating plasma cortisol levels throughout the medication period at the 200 mg. dose level (Table 3). Lower doses were less active. Neither the eosinophil index (Table 4) nor the fasting blood glucose levels (Table 5) were altered at anytime during the study.

As shown by the drawing oral administration of nivazol to female monkeys at a dose of 1000 mg/monkey/day for 15 days resulted in marked decreases in circulating cortisol levels while Medrol (50 mg/monkey/day) caused a lesser decrease in cortisol levels. Treatment with Medrol resulted in eosinopenia throughout the medication period but the eosinophil count remained within control limits during treatment with nivazol (Table 6). There was significant elevation in the fasting blood glucose levels in monkeys treated with Medrol while treatment with nivazol did not alter this parameter (Table 7).

TABLE 1

Comparative Effects of Nivazol and Medrol on the Endocrine Balance of Mature Female Rats

| | TREATMENT | | | | |
|---|---|---|---|---|---|
| | | Nivazol | | Medrol | |
| mg/kg/day × 14 po | 0[1] | 1.0 | 5.0 | 1.5 | 7.5 |
| No. of Rats | 8 | 8 | 8 | 8 | 8 |
| Body Weight (g) | | | | | |
| Initial | 203[2] | 203 | 203 | 203 | 203 |
| | ±2 | ±2 | ±2 | ±2 | ±2 |
| Final | 227 | 220 | 190 | 216 | 194 |
| | ±4 | ±2 | ±3 | ±3 | ±3 |
| Change (g/rat/day) | 1.7 | 1.2 | −0.9** | 0.9 | −0.6** |
| | ±0.3 | ±0.2 | ±0.2 | ±0.2 | ±0.2 |
| Feed Consumption | 16.0 | 16.1 | 15.2 | 15.3 | 14.2 |
| g/rat/day | ±0.5 | ±0.5 | ±0.7 | ±0.5 | ±0.5 |
| Organ Weights (mg) | | | | | |
| Adrenals | 69.6 | 55.2** | 30.9** | 54.7** | 48.6** |
| | ±1.7 | ±1.5 | ±2.1 | ±1.6 | ±2.4 |
| Thymus | 498.8 | 417.1 | 115.9** | 149.2** | 122.6** |
| | ±34.0 | ±22.8 | ±29.8 | ±11.1 | ±12.4 |
| Pituitary | 15.5 | 14.9 | 12.7 | 13.4 | 11.8 |
| | ±0.7 | ±0.5 | ±0.7 | ±1.0 | ±0.8 |

[1]Vehicle control, 1% gum tragacanth
[2]Mean ± SE
*Significantly different from the mean of the control group, p <0.01.
**Significantly different from the mean of the control group, p <0.001

TABLE 2

Comparative Effects of Nivazol and Medrol on Thymus Weight and Liver-Glycogen Deposition in Adrenalectromized Mature Male Rats

| | TREATMENT | | | | |
|---|---|---|---|---|---|
| | mg/kg/day × 5 po | | | | |
| | | Nivazol | | Medrol | |
| | 0[1] | 5 | 15 | 5 | 15 |
| No. of Rats | 10 | 10 | 10 | 10 | 10 |
| Body Weight (g) | | | | | |
| Initial | 246[2] | 246 | 246 | 246 | 246 |
| | ±2 | ±2 | ±3 | ±2 | ±3 |
| Final | 255 | 249 | 234** | 238** | 232** |
| | ±3 | ±4 | ±3 | ±2 | ±4 |
| Thymus Weight | 740 | 357** | 119** | 241** | 107** |
| (mg) | ±24 | ±31 | ±9 | ±15 | ±7 |
| Liver Glycogen | 2.04 | 5.97** | 26.7** | 6.19** | 17.3**[30] |
| (mg/g of Tissue) | ±0.05 | ±1.02 | ±2.7 | ±0.55 | ±0.7 |

[1]Vehicle control, 1% gum tragacanth.
[2]Mean ± SE.
**Significantly different from the mean of the control group, p <0.001.
+Significantly different from the mean of the group receiving Win 27,914 alone, p <0.01.

TABLE 3

Effect of Nivazol on Circulating Cortisol in the Mature Female Monkey

| Nivazol mg/monkey/day × 18 po[1] | PLASMA CORTISOL (ng/ml) | | | | | | | | | | | |
|---|---|---|---|---|---|---|---|---|---|---|---|---|
| | Pretreatment | | Treatment Day | | | | | | | | | |
| | | | 1 | | 2 | | 4 | | 8 | | 16 | |
| | AM | PM | AM | PM | AM | PM | AM | PM | AM | PM | AM | PM |
| 0[2] | 266 | 125 | 350 | 156 | 325 | 132 | 309 | 138 | 367 | 131 | 354 | 152 |
| | ±21 | ±17 | ±28 | ±17 | ±39 | ±15 | ±21 | ±17 | ±36 | ±15 | ±26 | ±17 |
| 50 | 314 | 135 | 344 | 110** | 317 | 110 | 269 | 94** | 325 | 101** | 344 | 141 |
| | ±26 | ±30 | ±14 | ±7 | ±21 | ±17 | ±35 | ±16 | ±35 | ±7 | ±36 | ±24 |
| 100 | 357 | 200 | 395 | 187 | 327 | 119 | 254 | 95 | 244 | 104 | 229 | 106 |
| | ±21 | ±34 | ±10 | ±35 | ±24 | ±20 | ±56 | ±20 | ±40 | ±17 | ±57 | ±28 |
| 200 | 335 | 172 | 368 | 104 | 275 | 78** | 48** | 23** | 224* | 57** | 174* | 65** |
| | ±29 | ±30 | ±35 | ±2 | ±25 | ±7 | ±11 | ±3 | ±36 | ±5 | ±58 | ±19 |

[1]Five monkeys per group.
[2]Vehicle control, 1% gum tragacanth.
[3]Mean ± SE.
*Significantly different from the overall AM mean (340 ± 8, n = 60) or PM (149 ± 8, n = 45) mean control value p <0.01.
**Significantly different from the overall AM or PM control value, p <0.001.

TABLE 4

Effect of Nivazol on the Eosinophil Index in Mature Female Monkeys

| Treatment[1] Nivazol mg/monkey/ day × 18 po | Pre-treatment | Treatment Day | | | |
|---|---|---|---|---|---|
| | | 1 | 2 | 4 | 8 | 16 |
| 0[3] | 13.3 | 11.5 | 9.7 | 13.3 | 9.5 | 14.7 |
| | ±1.2 | ±2.6 | ±1.7 | ±1.9 | ±1.7 | ±2.4 |
| 50 | 13.3 | 11.4 | 12.1 | 7.9 | 8.1 | 13.0 |
| | ±1.0 | ±1.4 | ±1.1 | ±1.2 | ±1.0 | ±2.0 |
| 100 | 13.3 | 14.8 | 12.5 | 11.1 | 8.5 | 13.2 |
| | ±1.2 | ±2.1 | ±1.9 | ±1.1 | ±1.7 | ±0.9 |
| 200 | 13.3 | 11.3 | 15.5 | 14.0 | 12.1 | 13.7 |
| | ±1.1 | ±0.5 | ±1.2 | ±1.0 | ±2.2 | ±1.4 |

[1]Five monkeys per group.
[2]Index = $\sqrt{x+1}$  Where x = the number of eosinophil/ul.
[3]Vehicle control, 1% gum tragacanth.

TABLE 5

Effect of Nivazol on Fasting Blood Glucose Levels in the Mature Female Monkey

| Treatment Nivazol mg/monkey/day × 18 po | No. of Monkeys | Fasting Blood Glucose (mg/dl) | |
|---|---|---|---|
| | | Pretreatment | Day 18 of Study |
| 0[1] | 5 | 92 ± 5[2] | 82 ± 4 |
| 50 | 5 | 91 ± 4 | 73 ± 3 |
| 100 | 5 | 84 ± 2 | 85 ± 4 |
| 200 | 5 | 92 ± 4 | 81 ± 5 |

[1]Vehicle control, 1% gum tragacanth
[2]Mean ± SE.

TABLE 6

Effect of Nivazol and Medrol on the Eosinophil Index in the Mature Female Monkey

| Treatment | | No. of Monkeys | Pretreatment | Eosinophil Index[1] Mean ± SE | | | | |
|---|---|---|---|---|---|---|---|---|
| Drug | mg/monkey/ day × 11 po | | | Treatment Day | | | | |
| | | | | 1 | 2 | 4[3] | 9 | 11 |
| — | 0[2] | 5 | 17.6 | 19.9 | 17.9 | 18.7 | 16.6 | 17.1 |
| | | | ±1.3 | ±1.8 | ±2.3 | ±1.2 | ±2.4 | ±1.1 |
| Medrol | 50 | 5 | 17.5 | 2.2** | 2.0** | 7.4** | 3.5** | 2.8** |
| | | | ±1.4 | ±0.5 | ±0.7 | ±1.1 | ±0.7 | ±0.8 |
| Nivazol | 1000 | 4 | 17.7 | 19.0 | 15.8 | 12.1 | 9.9 | 13.7 |
| | | | ±1.2 | ±1.8 | ±1.3 | ±1.5 | ±1.0 | ±0.9 |

[1]Index = $\sqrt{x+1}$  Where x = the number of eosinophil/ul
[2]Vehicle control, 1% gum tragacanth
[3]Eosinophils counted at 3 hours post drug rather than at 4 hours
**Significantly different from the mean of the control group, p <0.001

TABLE 7

Effect of Nivazol and Medrol on Fasting Blood Glucose Levels in the Mature Female Monkey

| Treatment Drug | mg/monkey/day × 15 po | No. of Monkeys | Fasting Blood Glucose (mg/dl) | | Eight Days after Last Treatment |
|---|---|---|---|---|---|
| | | | Day of Treatment | | |
| | | | 7 | 15 | |
| — | 0[1] | 5 | 87 ± 2[2] | 90 ± 3 | 90 ± 3 |
| Medrol | 50 | 5 | 103 ± 4* | 107 ± 4* | 91 ± 4 |
| Nivazol | 1000 | 4 | 86 ± 6 | 92 ± 4 | 90 ± 6 |

[1]Vehicle control, 1% gum tragacanth.
[2]Mean ± SE.
*Significantly different from mean of the control group, p <0.01.

Nivazol is prepared for use by incorporating it in an inert pharmaceutical carrier. The formulation is prepared by dissolving or suspending the steroid in a pharmaceutically acceptable liquid vehicle, e.g. aqueous ethanol, glycol, cottonseed oil solution or oil-water emulsion, gum tragacanth suspension, or the like; or by incorporating the steroid in unit dosage form as tablets or capsules either alone or in combination with conventional adjuvants, e.g. lactose, starch, silicon dioxide, talc, gum acacia, magnesium stearate, calcium carbonate and the like.

The following formulas are an actual formula for a 100-mg. capsule and a proposed formula for 50-mg. and 25-mg. capsules.

| Ingredient | Weight (mg.) |
|---|---|
| nivazol | 100.00 |
| lactose impalpable powder | 79.48 |
| starch | 80.00 |
| fumed silicon dioxide | 0.52 |
| Total Weight | 260.00 |
| nivazol | 50.00 |
| lactose impalpable powder | 124.40 |
| starch | 125.00 |
| fumed silicon dioxide | 0.60 |
| Total Weight | 300.00 |
| nivazol | 25.00 |
| lactose impalpable powder | 137.40 |
| starch | 137.00 |
| fumed silicon dioxide | 0.60 |

-continued

| Ingredient | Weight (mg.) |
|---|---|
| Total Weight | 300.00 |

We claim:

1. The method of suppressing pituitary-adrenal function without producing peripheral glucocorticoid effects in a person having an inappropriately high concentration of circulating corticoids and/or ACTH which comprises administering to the person an amount of (17α)-2'-(4-fluorophenyl)-2'H-pregna-2,4-dien-20-yno[3,2-c]pyrazol-17-ol effective in reducing the concentration of circulating corticoids and/or ACTH.

2. The method according to claim 1 wherein the daily dose of (17α)-2'-(4-fluorophenyl)-2'H-pregna-2,4-dien-20-yno-[3,2-c]pyrazol-17-ol is from 50 to 500 milligrams.

* * * * *